United States Patent
Cheshire et al.

(10) Patent No.: US 6,953,797 B2
(45) Date of Patent: *Oct. 11, 2005

(54) USE OF PHENYLHETEROALKYLAMINE DERIVATIVES

(75) Inventors: David Cheshire, Loughborough (GB); Stephen Connolly, Loughborough (GB); David Cox, Loughborough (GB); Ian Millichip, Loughborough (GB)

(73) Assignee: AstraZeneca AB, Söderälje (SE)

(*) Notice: Subject to any disclaimer, the term of this patent is extended or adjusted under 35 U.S.C. 154(b) by 49 days.

This patent is subject to a terminal disclaimer.

(21) Appl. No.: 10/204,808

(22) PCT Filed: Feb. 20, 2001

(86) PCT No.: PCT/SE01/00371

§ 371 (c)(1), (2), (4) Date: Aug. 22, 2002

(87) PCT Pub. No.: WO01/62721

PCT Pub. Date: Aug. 30, 2001

(65) Prior Publication Data

US 2003/0073685 A1 Apr. 17, 2003

(30) Foreign Application Priority Data

Feb. 23, 2000 (GB) ............................. 0004151

(51) Int. Cl.[7] .................. A61K 31/535; A61K 31/42; C07D 263/30; C07D 295/06; C07C 255/50
(52) U.S. Cl. .................. 514/238.2; 514/374; 514/524; 514/649; 548/235; 544/167; 558/418; 558/422
(58) Field of Search .................. 558/418, 422; 544/167; 548/23.5, 228

(56) References Cited

U.S. PATENT DOCUMENTS

| | | | |
|---|---|---|---|
| 4,296,126 A | 10/1981 | Nedelec et al. | |
| 4,314,081 A | 2/1982 | Molloy et al. | |
| 4,666,910 A | 5/1987 | Schneider et al. | |
| 4,902,710 A | 2/1990 | Foster et al. | |
| 6,743,939 B2 | 6/2004 | Birkinshaw et al. | |
| 2003/0139350 A1 * | 7/2003 | Larsen et al. ............. | 514/25 |

FOREIGN PATENT DOCUMENTS

| | | |
|---|---|---|
| DE | 29 07 217 A1 | 8/1979 |
| EP | 0 273 658 | 7/1988 |
| EP | 0 318 727 A2 | 6/1989 |
| EP | 0 399 504 A2 | 11/1990 |
| EP | 0 515 240 A1 | 11/1992 |
| EP | 0 571 685 A1 | 12/1993 |
| EP | 0 576 766 A1 | 1/1994 |
| EP | 0 661 266 A1 | 7/1995 |
| EP | 0 707 007 A1 | 4/1996 |
| GB | 765849 | 1/1957 |
| GB | 922600 | 4/1963 |
| GB | 1014348 | 12/1965 |
| GB | 2 060 620 A | 5/1981 |
| GB | 2 060 621 A | 5/1981 |
| GB | 2 060 622 A | 5/1981 |
| JP | 51044934 B4 | 12/1976 |
| JP | 52-941 | 1/1977 |
| JP | 52000941 B4 | 1/1977 |
| WO | WO 92/19210 | 11/1992 |
| WO | WO 99/10339 | 3/1999 |
| WO | WO 99/11620 | 3/1999 |
| WO | WO 99/38514 | 8/1999 |
| WO | WO 99/62883 | 12/1999 |
| WO | WO 00/27842 | 5/2000 |
| WO | WO 00/58305 | 10/2000 |
| WO | WO 02/20484 | 3/2002 |
| WO | WO 02/30899 | 4/2002 |

OTHER PUBLICATIONS

U.S. Appl. No. 10/204,845, filed Aug. 22, 2002, Cheshire et al.
U.S. Appl. No. 10/204,742, filed Oct. 18, 2002, Cheshire et al.
U.S. Appl. No. 10/476,958, filed Jan. 8, 2004, Birkinshaw et al.
U.S. Appl. No. 10/483,140, filed Jan. 8, 2004, Birkinshaw et al.
Chemical Abstracts, CAPLUS accession No. 1998: 394854 (Zhongguo Yaoke Daxue Xuebao, 1998, 29, 81–91).
Chemical Abstracts, CAPLUS accession No. 1968: 28182 (J. Med. Chem., 1968, 11, 95–97).
Chemical Abstracts, CAPLUS accession No. 1997: 534782 (Zhongguo Yaoke Huaxue Zazhi, 1997, 7, 1–8).

(Continued)

Primary Examiner—Johann Richter
Assistant Examiner—Ebenezer Sackey
(74) Attorney, Agent, or Firm—Fish & Richardson P.C.

(57) ABSTRACT

There is disclosed the use of a compound of formula (I), wherein $R^1$, $R^2$, X, Y, V, W and Z are as defined in the specification, and pharmaceutically acceptable salts, enantiomers or racemates thereof, in the manufacture of a medicament, for the treatment or prophylaxis of diseases or conditions in which inhibition of nitric oxide synthase activity is beneficial. Certain novel compounds of formula (Ia) and pharmaceutically acceptable salts thereof, and enantiomers and racemates thereof are disclosed; together with processes for their preparation, compositions containing them and their use in therapy. The compounds of formulae (I) and (Ia) are inhibitors of the enzyme nitric oxide synthase and are thereby particularly useful in the treatment or prophylaxis of inflammatory disease

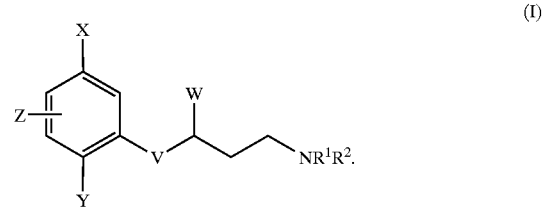

(I)

7 Claims, No Drawings

OTHER PUBLICATIONS

Chemical Abstracts, CAPLUS accession No. 1999: 659361 (WO 99/51575).
Chemical Abstracts, CAPLUS accession No. 1967: 499505 (J. Chem. Soc. B, 1967, 859–866).
Chemical Abstracts, CAPLUS accession No. 1994: 579176 (Tetrahedron Letters, 1994, 35, 4585–4586).
Chemical Abstracts, CAPLUS accession No. 1968: 29366 (Probl. Poluch. Poluprod. Prom. Org. Sin., 1967, 90–97).
Chemical Abstracts, CAPLUS accession No. 1995: 664999 (DE 4 331 179).
Chemical Abstracts, CAPLUS accession No. 1995: 913361 (WO 95/15954).
Chemical Abstracts, CAPLUS accession No. 1981: 121503 (DE 2 905 877).
Chemical Abstracts, CAPLUS accession No. 1990: 35674 (JP 01168666).
Chemical Abstracts, CAPLUS accession No. 1978: 169760 (JP A2 52153922).
Chemical Abstracts, CAPLUS accession No. 1977: 189458 (JP 51044934).
Chemical Abstracts, CAPLUS accession No. 1996: 113480 (SU 1824396).
Chemical Abstracts, 1965, vol. 62, 16781 (J. Med. Chem. 1965, 8, 356–367).
Chemical Abstracts, 1958, vol. 52, 11069 (J. Am. Chem. Soc., 1958, 80, 162–164).
Chemical Abstracts, 1966, vol. 65, 2181 (Neth. Appln. 6,508,754).
S. J. Yan et al., "Potential causal prophylactic antimalarial agents. Synthesis of quinoxaline, benzimidazole, and alkoxybenzene derivatives containing a novoldiamine moiety", J. Heterocycl. Chem., 297–300, (1978).

* cited by examiner

USE OF PHENYLHETEROALKYLAMINE DERIVATIVES

CROSS REFERENCE TO RELATED APPLICATIONS

The present application is a national phase application under 35 U.S.C. Section 371 filed from International Patent Application PCT/SE01/00371, filed 20 Feb. 2001, which claims priority to United Kingdom patent application Ser. No. 0004151.7, filed 23 Feb. 2000. The contents of these applications are incorporated herein by reference in their entirety.

FIELD OF THE INVENTION

The present invention relates to the use of phenylheteroalkylamine derivatives as inhibitors of the enzyme nitric oxide synthase. Certain novel phenylheteroalkylamine derivatives are also disclosed together with processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221–230).

Considerable effort has been expended in efforts to identify compounds that act as specific inhibitors of one or more isoforms of the enzyme nitric oxide synthase. The use of such compounds in therapy has also been widely claimed.

U.S. Pat. No. 4,902,710 discloses novel compounds of formula

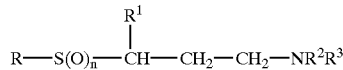

wherein $R^1$ represents phenyl, substituted phenyl, C5 to 7 cycloalkyl, thienyl, halothienyl, (C1 to 4 alkyl)-substituted-thienyl, furanyl, pyridyl or thiazolyl; $R^2$ and $R^3$ are each independently H or methyl; n is 0, 1 or 2; and R can be, amongst other groups, substituted phenyl. Said compounds are potent and selective inhibitors of serotonin and norepinephrine uptake and are thereby claimed to be useful in the treatment of human diseases such as anxiety, depression and obesity.

The present invention relates to the surprising finding that a group of phenylheteroalkylamine derivatives, including some compounds that are within the generic scope of U.S. Pat. No. 4,902,710, are inhibitors of the enzyme nitric oxide synthase.

DISCLOSURE OF THE INVENTION

According to the present invention, there is provided the use of a compound of formula (I)

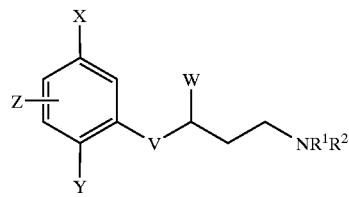

wherein:
X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;
m and p independently represent an integer 0, 1 or 2;
Z represents H or fluoro;
V represents $S(O)_n$ or $NR^3$;
W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;
$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;
$R^3$ represents H or C1 to 4 alkyl;
$R^4$, $R^5$ $R^6$, $R^7$, $R^9$ and $R^{10}$ independently represent H or C1 to 4 alkyl;
$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
$R^{11}$ and $R^{12}$ independently represent H or C1 to 4 alkyl;
n represents an integer 0, 1 or 2;
or a pharmaceutically acceptable salt, enantiomer or racemate thereof, in the manufacture of a medicament, for the treatment or prophylaxis of diseases or conditions in which inhibition of nitric oxide synthase activity is beneficial.

In another aspect the invention provides the use of a compound of formula (I) or a pharmaceutically acceptable salt, enantiomer or racemate thereof, in the manufacture of a medicament, for the treatment or prophylaxis of diseases or conditions in which inhibition of the inducible isoform of the enzyme nitric oxide synthase activity is beneficial.

A more particular aspect of the invention provides the use of a compound of formula (I) or a pharmaceutically acceptable salt, enantiomer or racemate thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer or racemate thereof.

Further, according to the invention, there is also provided a method of treating, or reducing the risk of, diseases or conditions in which inhibition of the activity of the inducible isoform of the enzyme nitric oxide synthase is beneficial which comprises administering to a person suffering from or at risk of, said disease or condition, a therapeutically effective amount of a compound of formula (I) or a pharmaceutically acceptable salt, enantiomer or racemate thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer or racemate thereof.

In another aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of diseases or conditions in which inhibition of nitric oxide synthase activity is beneficial.

In another preferred aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of diseases or conditions in which inhibition of the inducible isoform of the enzyme nitric oxide synthase activity is beneficial.

In another more particular aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of inflammatory disease.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer or racemate thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer or racemate thereof in combination with a COX-2 inhibitor.

In one preferred embodiment, V represents S. In another preferred embodiment, V represents NH.

In another preferred embodiment, X and Y independently represent Br, Cl, $CH_3$, $CF_3$ or CN. It is particularly preferred that X represents Br, Cl or $CF_3$. It is also particularly preferred that Y represents Cl or CN.

Preferably, W represents an optionally substituted five or six membered aromatic heterocyclic ring containing 1 to 3 heteroatoms independently selected from O, S and N.

Preferably, $R^1$ and $R^2$ independently represent H or C1 to 4 alkyl optionally substituted by C1 to 4 alkoxy or hydroxy. More preferably, $R^1$ and $R^2$ independently represent H or methyl.

The use of the following compounds of formula (I) and pharmaceutically acceptable salts, enantiomers or racemates thereof is specifically included within the invention:

3-[(2,5-dichlorophenyl)thio]-N-methyl-benzenepropanamine;
2-[[3-(dimethylamino-1-phenylpropyl]amino]-4-(trifluoromethyl)-benzonitrile;
4-chloro-2-[3-(methylamino)-1-phenylpropyl]amino]-benzonitrile;
4-chloro-2-{[3-(methylamino)-1-phenylpropyl]thio}benzonitrile;
4-bromo-2-{[3-(methylamino)-1-phenylpropyl]thio}benzonitrile;
3-[(2,5-dichlorophenyl)sulphonyl]-N-methylbenzenepropanamine;
(1R)-$N^1$-[2-chloro-5-(trifluoromethyl)phenyl]-$N^3$-methyl-1-phenyl-1,3-propanediamine;
2-[[(1R)-3-amino-1-phenylpropyl]amino]-4-chloro-5-fluorobenzonitrile;
4-chloro-5-fluoro-2-[[(1R)-3-(methylamino)-1-phenylpropyl]amino]benzonitrile;
N-(5-chloro-2-nitrophenyl)-1-phenyl-3-(morpholin-1-yl)propanamine;
2-[[(1R)-3-amino-1-phenylpropyl]thio]-4-chlorobenzonitrile;
2-[[(1R)-3-amino-1-phenylpropyl]thio]-4-(trifluoromethyl)benzonitrile;
γ-[(2,5-dimethylphenyl)thio]-N-methyl-benzenepropanamine;
4-chloro-2-[methyl[3-(methylamino)-1-phenylpropyl]amino]benzonitrile;
($γ^2$R)-γ-[(2,5-dichlorophenyl)thio]-2-thiazolepropanamine;
γ-[(2,5-dichlorophenyl)thio]-2-oxazolepropanamine.

Unless otherwise indicated, the term "C1 to 4 alkyl" referred to herein denotes a straight or branched chain alkyl group having from 1 to 4 carbon atoms. Examples of such groups to include methyl, ethyl, n-propyl, i-propyl, n-butyl, i-butyl and t-butyl.

The term "C1 to 6 alkyl" is to be interpreted analogously.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

Examples of a "C1 to 4 alkyl or C1 to 4 alkoxy optionally further substituted by one or more fluorine atoms" include $CF_3$, $CF_3CF_2$, $CF_3CH_2$, $CH_2FCH_2$, $CH_3CF_2$, $CF_3CH_2CH_2$, $OCF_3$ and $OCH_2CF_3$.

Unless otherwise indicated, the term "halogen" referred to herein denotes fluoro, chloro, bromo and iodo.

Examples of a 4 to 8 membered saturated azacyclic ring optionally incorporating one further heteroatom selected from O, S or N include pyrrolidine, piperidine, piperazine, morpholine and perhydroazepine.

Examples of a five or six membered aromatic heterocyclic ring containing 1 to 3 heteroatoms independently selected from O, S and N include furan, thiophene, pyridine, thiazolyl, imidazole, oxazole, triazole, oxadiazole, thiadiazole and pyrimidine.

Examples of a five or six membered saturated heterocyclic ring containing 1 to 3 heteroatoms independently selected from O, S and N include pyrrolidine, tetrahydrofuran, piperidine and piperazine.

Certain compounds of formula (I) are novel. Therefore a further aspect of the invention provides a compound of formula (Ia)

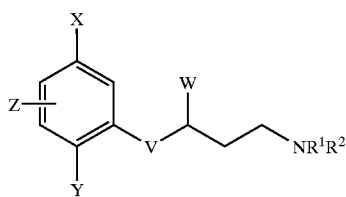

(Ia)

wherein
X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;
m and p independently represent an integer 0, 1 or 2;
Z represents H or fluoro;
V represents S(O), or $NR^3$;
W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;
$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl C1 to 4 alkoxy, $CF_3$, $OCF_3$, CN or $NO_2$;
or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;
$R^3$ represents H or C1 to 4 alkyl;
$R^4$, $R^5$ $R^6$, $R^7$, $R^9$ and $R^{10}$ independently represent H or C1 to 4 alkyl;
$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally Per substituted by halogen, C1 to 4 alkyl, C1 to 4 alkoxy, $CF_3$, $OCF_3$, CN or $NO_2$;
$R^{11}$ and $R^{12}$ independently represent H or C1 to 4 alkyl;
n represents an integer 0, 1 or 2;
or a pharmaceutically acceptable salt, enantiomer or racemate thereof, with the proviso that when V represents $S(O)_n$; and $R^1$ and $R^2$ independently represent H or methyl; and W represents phenyl, optionally substituted by halogen, C1 to 4 alkyl, C1 to 3 alkoxy or $CF_3$; or W represents thienyl, halothienyl, (C1 to 4 alkyl)-substituted-thienyl, furanyl, pyridyl or thiazolyl; then at least one of X and Y represents $OCF_3$, CN, C≡CH, $S(O)_mCH_3$, $S(O)_pCF_3$, $NO_2$ or NHCHO.

According to the invention there is also provided a compound of formula (Ia), or a pharmaceutically acceptable salt, enantiomer or racemate thereof, for use as a medicament.

In one preferred embodiment, V in formula (Ia) represents S. In another preferred embodiment, V in formula (Ia) represents NH.

In another preferred embodiment, X and Y in formula (Ia) independently represent Br, Cl, $CH_3$, $CF_3$ or CN. It is particularly preferred that X represents Br, Cl or $CF_3$. It is also particularly preferred that Y represents Cl or CN.

Preferably, W in formula (Ia) represents an optionally substituted five or six membered aromatic heterocyclic ring containing 1 to 3 heteroatoms independently selected from O, S and N.

Preferably, $R^1$ and $R^2$ in formula (Ia) independently represent H or C1 to 4 alkyl optionally substituted by C1 to 4 alkoxy or hydroxy. More preferably, $R^1$ and $R^2$ independently represent H or methyl.

Particular compounds of formula (Ia) include:

2-[[3-(dimethylamino)-1-phenylpropyl]amino]-4-(trifluoromethyl)-benzonitrile;
4-chloro-2-[3-(methylamino)-1-phenylpropyl]amino]-benzonitrile;
4-chloro-2-{[3-(methylamino)-1-phenylpropyl]thio}benzonitrile;
4-bromo-2-{[3-(methylamino)-1-phenylpropyl]thio}benzonitrile;
(1R)-$N^1$-[2-chloro-5-(trifluoromethyl)phenyl]-$N^3$-methyl-1-phenyl-1,3-propanediamine;
2-[[(1R)-3-amino-1-phenylpropyl]amino]-4-chloro-5-fluorobenzonitrile;
4-chloro-5-fluoro-2-[[(1R)-3-(methylamino)-1-phenylpropyl]amino]benzonitrile;
N-(5-chloro-2-nitrophenyl)-1-phenyl-3-(morpholin-1-yl)propanamine;
2-[[(1R)-3-amino-1-phenylpropyl]thio]-4-chlorobenzonitrile;
2-[[(1R)-3-amino-1-phenylpropyl]thio]-4-(trifluoromethyl)benzonitrile;
4-chloro-2-[methyl[3-(methylamino)-1-phenylpropyl]amino]benzonitrile;
γ-[(2,5-dichlorophenyl)thio]-2-oxazolepropanamine;

and pharmaceutically acceptable salts, enantiomers or racemates thereof.

According to the invention, we further provide a process for the preparation of compounds of formula (Ia), or a pharmaceutically acceptable salt, enantiomer or racemate thereof which comprises:

(a) reaction of a compound of formula (II)

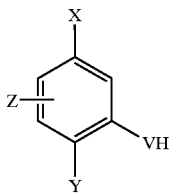

wherein X, Y, V and Z are as defined in formula (Ia), with a compound of formula (III)

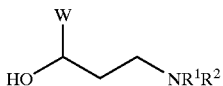

wherein W, R¹ and R² are as defined in formula (Ia); or (b) reaction of a compound of formula (IV)

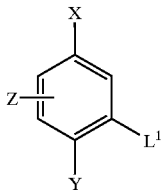

wherein X, Y and Z are as defined in formula (Ia) and $L^1$ represents a leaving group, with a compound of formula (V)

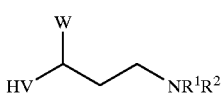

wherein $R^1$, $R^2$, V and W are as defined in formula (Ia); or (c) reaction of a compound of formula (VI)

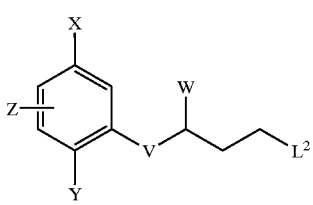

wherein X, Y, V, W and Z are as defined in formula (Ia) and $L^2$ is a leaving group, with a compound of formula (VII)

wherein $R^1$ and $R^2$ are as defined in formula (Ia); or (d) reaction of a compound of formula (II)

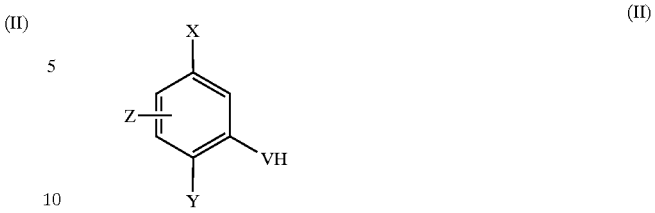

wherein X, Y. V and Z are as defined in formula (Ia), with a compound of formula (VIII)

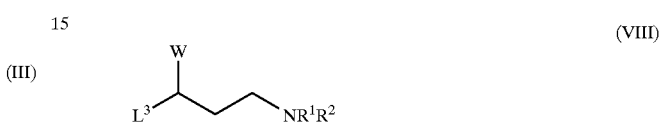

wherein $R^1$, $R^2$ and W are as defined in formula (Ia) and $L^3$ is a leaving group; or (e) reduction of a compound of formula (IX)

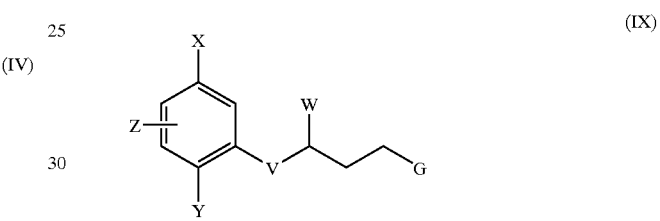

wherein X, Y, V, W and Z are as defined in formula (Ia) and G represents a group that upon reduction is converted into a group $NR^1R^2$;

and where necessary converting the resultant compound of formula (Ia), or another salt thereof, into a pharmaceutically acceptable salt thereof; or converting the resultant compound of formula (Ia) into a further compound of formula (Ia); and where desired converting the resultant compound of formula (Ia) into an optical isomer thereof.

In process (a), the reactants (II) and (III) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine.

In process (b), the reaction is performed by treating a nucleophile of formula (V) with an electrophile of formula (IV) in an inert solvent. Suitable leaving groups $L^1$ include halides, particularly fluoride. The reaction is generally performed in the presence of a non-nucleophilic base such as sodium hydride. Suitable organic solvents are those such as N-methyl-2-pyrrolidinone, tetrahydrofuran, C1 to 4 alcohols and dimethylsulfoxide. The reaction is generally conducted at a temperature between 0° C. and the boiling point of the solvent.

Alternatively, in process (b), the reaction will take place using an appropriate palladium source such as palladium (II) acetate in the presence of a suitable phosphine ligand such as BINAP.

In process (c), the amination reaction is performed by reacting a compound of formula (VI) with an amine (VII) in an inert solvent. Suitable leaving groups $L^2$ include sulfonate, trifluorosulfonate, tosylate and halides selected from the group chloride, bromide or iodide. The nucleophile can be a primary or secondary amine in the presence of a base. This base can be either an excess of the amine nucleophile or can be an additive to the reaction mixture. Potential basic additives are metal carbonate, especially alkali metal carbonates, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols.

In process (d), the reaction is performed by treating a nucleophile of formula (II) with an electrophile of formula (VIII) in an inert solvent. Suitable leaving groups $L^3$ include halides, particularly chloride or bromide. The reaction is generally performed in the presence of a non-nucleophilic base such as sodium hydride. Suitable organic solvents are those such as N-methyl-2-pyrrolidinone, tetrahydrofuran, C1 to 4 alcohols and dimethylsulfoxide. The reaction is generally conducted at a temperature between 0° C. and the boiling point of the solvent.

In process (e), G preferably represents an azido ($N_3$) group. The required reduction may then be achieved by treating a compound of formula (IX) with a suitable reducing agent such as Sn(II) or triphenylphosphine. Preferably the reducing agent is triphenylphosphine and the reduction is carried out in a suitable inert solvent such as tetrahydrofuran.

It will be apparent to a person skilled in the art that in the above processes it may be desirable or necessary to protect an amine, hydroxyl or other potentially reactive group. Suitable protecting groups and details of processes for adding and removing such groups may be found by reference to the standard text "Protecting Groups in Organic Synthesis", 2nd Edition (1991) by Greene and Wuts. In one preferred embodiment, amine groups are protected as carbamate derivatives, for example, as t-butyloxycarbamates. Thus, compounds of formula (Ia) in which $R^1$ is H are conveniently prepared by removal of a carbamate protecting group from a corresponding compound of formula (Ia) wherein $R^1$ is a carbamate group, especially a t-butyloxycarbamate group. Removal of the carbamate group is conveniently effected using hydrogen chloride in dioxan.

The present invention includes compounds of formula (Ia) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (Ia) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Certain novel intermediates of formulae (III), (V), (VI), (VIII) and (IX) form another aspect of the invention.

Compounds of formula (III) may be prepared by reaction of a compound of formula (X)

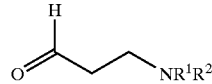

(X)

wherein $R^1$ and $R^2$ are as defined in formula (Ia), with an organometallic derivative, W-M, wherein W is as defined in formula (Ia) and M represents a metallic residue such as lithium or magnesium-halide.

Compounds of formula (IX) may be prepared by:
(a) reacting a compound of formula (II), as defined above, with a compound of formula (XI)

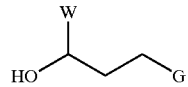

(XI)

wherein W and G are as defined above; or
(b) reacting a compound of formula (IV), as defined above, with a compound of formula (XII)

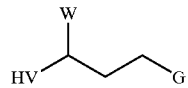

(XII)

wherein V, W and G are as defined above.

Compounds of formulae (II), (IV), (VII), (X), (XI) and (XII) are either known or may be prepared using known methods. Some such methods are illustrated within the Examples that are included herein. Other suitable methods will be readily apparent to the man skilled in the art.

Intermediate compounds may be used as such or in protected form. Protecting groups and details of processes for their removal may be found by reference to the standard text "Protecting groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula (Ia) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (Ia), and their pharmaceutically acceptable salts, enantiomers and racemates, are useful because they possess pharmacological activity in animals. In particular, the compounds of formulae (I) and (Ia) are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. They may also have utility as inhibitors of the neuronal isoform of the enzyme nitric oxide synthase.

The compounds of formulae (I) and (Ia) and their pharmaceutically acceptable salts, enantiomers and racemates are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis, glaucoma and conjunctivitis;

lung disorders in which inflammation is involved, for example, asthma, bronchitis, chronic obstructive pulmonary disease, pigeon fancier's disease, farmer's lung, acute respiratory distress syndrome;

bacteraemia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

By virtue of their pharmacological activity as inhibitors of the enzyme nitric oxide synthase, the compounds will also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease and pain.

The compounds of formulae (I) and (Ia) and their pharmaceutically acceptable salts, enantiomers and racemates may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formulae (I) and (Ia) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, Korsakoff's disease, imbecility relating to a cerebral vessel disorder, sleeping disorders, schizophrenia, autism, seasonal affective disorder, jet-lag and septic shock. Compounds of formulae (I) and (Ia) may also be expected to show activity in the prevention and reversal of drug addiction or tolerance such as tolerance to opiates and diazepines, treatment of migraine and other vascular headaches, neurogenic inflammation, in the treatment of gastrointestinal motility disorders, cancer and in the induction of labour.

We are particularly interested in the conditions stroke, Alzheimer's disease, Parkinson's disease, multiple sclerosis, schizophrenia, migraine, cancer and septic shock.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (Ia), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (Ia), or a pharmaceutically acceptable salt, enantiomer or racemate thereof.

There is also provided a process for the preparation of such a pharmaceutical composition which comprises mixing the ingredients.

The compounds of formulae (I) and (Ia), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

3-[(2,5-Dichlorophenyl)thio]-N-methyl-benzenepropanamine fumarate 2,5-Dichlorobenzenethiol (394 mg, 2.2 mmol) and 3-chloro-N-methyl-benzenepropanamine hydrochloride (440 mg, 2.0 mmol) were added sequentially to an ethanolic solution of sodium ethoxide [prepared from sodium (140 mg, 6.0 mmol)] in dry ethanol (32 ml) and the mixture heated under reflux with stirring for 1.5 h. The reaction mixture was cooled, evaporated, and the residue partitioned between water and ethyl acetate. The organic layer was separated, washed with brine and dried over magnesium sulphate. The solvent was evaporated and the residue eluted down a flash chromatography column using 10% methanol/ dichloromethane as eluent to give 320 mg of the product as the free base. This oil was dissolved in dry ethanol (10 ml) and treated with fumaric acid (114 mg). The mixture was heated under reflux with stirring for 0.5 h. The solvent was evaporated and the residual solid was triturated with acetonitrile to give 410 mg (46%) of the title compound as a cream solid.

MS APCI+ve$^m$/z 326 ([M+H]$^+$).

$^1$H NMR 300 MHz (d$_6$-DMSO) 7.45 (4H, m), 7.35 (2H, t), 7.25 (2H, m), 6.45 (2H, s), 4.82 (1H, t), 2.78 (1H, m), 2.65 (1H, m), 2.42 (3H, s), 2.22 (2H, m).

EXAMPLE 2

2-[[3-(Dimethylamino)-1-phenylpropyl]amino]-4-(trifluoromethyl)-benzonitrile

2-Fluoro-4-(trifluoromethyl)benzonitrile (0.15 ml, 1.1 mmol) and N$^3$, N$^3$-dimethyl-1-phenyl-1,3-propanediamine (420 mg, 2.4 mmol) in n-butanol (0.5 ml) were stirred and heated under reflux for 20 h. The crude reaction mixture was applied to a silica column and the product eluted with 50% isohexane-diethyl ether. The title compound was isolated as a pale yellow coloured solid (330 mg, 86%).

MS APCI+ve$^m$/z 348 ([M+H]$^+$).

$^1$H NMR 300 MHz (CDCl$_3$) 8.94 (1H, d), 7.4–7.16 (6H, m), 6.67 (1H, dd), 6.39 (1H, s), 4.59 (1H, q), 2.46–2.38 (1H, m), 2.31–2.24 (7H, m), 2.14–2.07 (1H, m), 1.8–1.73 (1H, m).

EXAMPLE 3

4-Chloro-2-[3-(methylamino)-1-phenylpropyl]amino]-benzonitrile a) 4-Chloro-2-[(3-hydroxy-1-phenylpropyl)amino]-benzonitrile A mixture of 3-amino-3-phenyl-1-propanol (1 g, 6.6 mmol), 4-chloro-2-fluorobenzonitrile (1 g, 6.4 mmol) and N,N-diisopropylethylamine (1.2 ml, 6.9 mmol) was stirred and heated at 140° C. for 5 h. The crude reaction mixture was cooled and purified on silica gel (ether/isohexane 1:4). The product was isolated as a colourless solid (1.1 g, 58%), m.p. 88–90° C.

MS APCI+ve$^m$/z 287 ([M+H]$^+$).

$^1$H NMR 300 MHz (d$_6$-DMSO) 7.5–7.2 (6H, m), 7.05 (1H, d), 6.63 (1H, dd), 6.51 (1H, d), 4.9 (1H, t), 4.73 (1H, q), 3.49 (2H, q), 2.1–1.88 (2H, m).

b) 4-Chloro-2-[(3-iodo-1-phenylpropyl)amino]-benzonitrile

To a solution of triphenylphosphine (1.83 g, 6.98 mmol) in dry tetrahydrofuran (30 ml) at 0° C. and under an atmosphere of nitrogen was added diethyl azodicarboxylate (1.2 g, 6.9 mmol) dropwise. After 20 minutes, lithium iodide and 4-chloro-2-[(3-hydroxy-1-phenylpropyl)amino]-benzonitrile (0.8 g, 2.79 mmol) were added to the mixture and stirring was continued for 5 h. The mixture was then concentrated to dryness, and the residue purified on silica (ether/isohexane 1:4). The title compound was isolated as a colourless solid (0.35 g, 32%).

$^1$H NMR 400 MHz (CDCl$_3$) 7.41–7.28 (6H, m), 6.65 (1H, d), 6.5 (1H, d), 4.94 (1H, br d), 4.6 (1H, q), 3.28–3.23 (1H, m), 3.1–3.04 (1H, m), 2.43–2.26 (2H, m).

c) 4-Chloro-2-[3-(methylamino)-1-phenylpropyl]amino]-benzonitrile

To a solution of methylamine (3 ml) in methanol (20 ml), was added 4-chloro-2-[(3-iodo-1-phenylpropyl)amino]-benzonitrile (0.35 g, 0.88 mmol). The mixture was stirred at ambient temperature for 20 h, then concentrated to dryness. The residue was purified by chromatography on silica gel (7N methanolic ammonia/dichloromethane, 1:9) to afford the title compound as a pale pink coloured solid (169 mg, 64%), m.p. 119–120° C.

MS APCI+ve$^m$/z 300/302 ([M+H]$^+$).

$^1$H NMR 300 MHz (CDCl$_3$) 8.22 (1H, d), 7.37–7.24 (6H, m), 6.52 (1H, dd), 6.27 (1H, d), 4.58 (1H, q), 2.8–2.66 (2H, m), 2.48 (3H, s), 2.14–2.05 (1H, m), 1.89–1.8 (1H, m).

EXAMPLE 4

4-Chloro-2-{[3-(methylamino)-1-phenylpropyl]thio}benzonitrile hydrochloride a) [3-(Acetylthio)-3-phenypropyl]methylcarbamic acid, 1,1-dimethylethyl ester To a stirred solution of triphenylphosphine (1.13 g, 4.32 mmol) in dry tetrahydrofuran (12 ml) was added diisopropyl azodicarboxylate (0.88 ml, 4.32 mmol) dropwise with stirring at 0° C. under nitrogen. After 0.5 h, a solution of (3-hydroxy-3-phenylpropyl)carbamic acid 1,1-dimethylethyl ester (0.572 g, 2.16 mmol) and thiolacetic acid (0.31 ml, 4.34 mmol) in dry tetrahydrofuran (10 ml) was added slowly at 0° C. The mixture was stirred at this temperature for 1 h, then stirred at room temperature overnight. The mixture was evaporated, and then eluted down a flash chromatography column using ether/isohexane (1:9) as eluent to give the product (420 mg, 60%) as a cream coloured solid.

MS APCI+ve$^m$/z 224 ([M+H]$^+$).

b) 4-Chloro-2-{[3-(methylamino)-1-phenylpropyl]thio]benzonitrile hydrochloride

[3-(Acetylthio)-3-phenylpropyl]methylcarbamic acid 1,1-dimethylethyl ester (300 mg, 0.928 mmol) in ethanol (20 ml) was treated with sodium hydroxide in water (5 ml) followed by 4-chloro-2-fluorobenzonitrile (144 mg, 0.928 mmol) and the mixture stirred at room temperature under nitrogen overnight. The reaction mixture was heated under reflux for 0.5 h, cooled, poured into water and extracted with ethyl acetate which was washed with brine and dried over magnesium sulphate. The solvent was evaporated and the residue eluted down a flash chromatography column using ether/isohexane (3:7) as eluent to give 160 mg of the carbamate protected product as a colourless oil. This material was stirred with 4M hydrogen chloride in dioxan (6 ml) for 1.5 h, evaporated, triturated with ether to give the title compound (122 mg, 37%) as a colourless solid.

MS APCI+ve$^m$/z 317 ([M+H]$^+$).

$^1$H NMR 300 MHz (d$_6$-DMSO) 8.76 (2H, brs), 7.83 (1H, d), 7.71 (1H, d), 7.48 (1H, d of d), 7.43–7.26 (5H, m), 4.96 (1H, t), 2.94 (1H, br m), 2.75 (1H, br m), 2.50 (3H, s), 2.28 (2H, m).

EXAMPLE 5

4-Bromo-2-{[3-(methylamino)-1-phenylpropyl]thio}benzonitrile oxalate

Prepared by the method of Example 5 using [3-(acetylthio)-3-phenylpropyl]methylcarbamic acid 1,1-dimethylethyl ester and 4-bromo-2-fluorobenzonitrile to give the title compound which was isolated as the oxalate salt.

MS APCI+ve $^m/z$ 363 ([M+H]$^+$).

$^1$H NMR 300 MHz (d$_6$-DMSO) 7.77 (1H, d), 7.73 (1H, s), 7.62 (1H, d of d), 7.41–7.26 (6H, m), 4.87 (1H, t), 2.97 (1H, m), 2.75 (1H, m), 2.53 (3H, s), 2.27 (2H, m).

EXAMPLE 6

3-[(2,5-Dichlorophenyl)sulphonyl]-N-methylbenzenepropanamine trifluoroacetate

The product from Example 1 (90 mg, 0.203 mmol) was stirred as a suspension in a 1:1 mixture of methanol/water (1 ml) under nitrogen at room temperature. Oxone® (375 mg, 0.61 mmol) was then added and the reaction mixture stirred for 4.5 h. The reaction was neutralised with sodium bicarbonate and extracted with dichloromethane which was dried over anhydrous sodium sulphate. The solvent was evaporated, the residue purified by reverse phase HPLC and the clean fractions freeze-dried to give the required product (8 mg, 8%) as the trifluoroacetate salt.

MS APCI+ve$^m/z$ 358 ([M+H]$^+$).

$^1$H NMR 300 MHz (d$_6$-DMSO) 7.78 (2H, m), 7.54 (1H, m), 7.36–7.26 (5H, m), 4.98 (1H, d of d), 3.30 (3H, s), 2.97 (1H, m), 2.64 (1H, m), 2.52 (2H, m).

EXAMPLE 7

(1R)-N$^1$-[2-Chloro-5-(trifluoromethyl)phenyl]-N$^3$-methyl-1-phenyl-1,3-propanediamine oxalate a) N-[2-Chloro-5-(trifluoromethyl)phenyl]-α-[2-[[(1,1-dimethylethyl) dimethylsilyl]oxy]ethyl]-(α$^1$R)-benzenemethanamine 2,2'-Bis(diphenylphosphino)-1,1'-binaphthyl (BINAP) (32.3 mg, 0.052 mmol) and palladium (II) acetate (23.3 mg, 0.104 mmol) were stirred at room temperature in toluene (5 ml) for 10 minutes. 2-Bromo-1-chloro-4-(trifluoromethyl) benzene (270 mg, 1.25 mmol) was added and the resulting mixture stirred for a further 10 minutes. (α$^1$R)-α-{2-[[(1,1-Dimethylethyl)dimethylsilyl]oxy]ethyl}benzenemethanamine (330 mg, 1.25 mmol) was added, and after another 10 minutes sodium tert-butoxide (140 mg, 1.45 mmol) was added and the reaction mixture heated to 120° C. overnight. The reaction was cooled, diluted with ether, filtered through celite and the filtrate evaporated to give 400 mg of crude product which was used directly in the next step.

b) (γ$^1$R)-γ-{[2-Chloro-5-(trifluoromethyl)phenyl]amino}benzenepropanol

The crude product from Example 7(a) (400 mg) was dissolved in tetrahydrofuran (10 ml) and tetrabutylammonium fluoride (1M solution in tetrahydrofuran; 1.87 ml) was added at room temperature. The mixture was stirred for 5 h, evaporated and the residue partitioned between ethyl acetate and water. The aqueous layer was separated and extracted with more ethyl acetate (2×), and the extracts combined and dried over anhydrous sodium sulphate. The solvent was evaporated and the residue eluted down a flash chromatography column using 10% methanol/dichloromethane as eluent to give product (148 mg) as a colourless oil.

$^1$H NMR 300 MHz (d$_6$-DMSO) 7.48 (1H, d), 7.35 (4H, m), 7.22 (1H, t), 6.83 (1H, d), 6.65 (1H, s), 6.51 (1H, d), 4.88 (1H, m), 4.70 (1H, m), 3.52 (2H, m), 2.00 (2H, m).

c) (1R)-N$^1$-[2-Chloro-5-(trifluoromethyl)phenyl]-N$^3$-methyl-1-phenyl-1,3-propanediamine oxalate The product of Example 7(b) (148 mg, 0.449 mmol) and triphenylphosphine (141 mg, 0.539 mmol) were stirred together in dry tetrahydrofuran (10 ml) at 0° C. N-iodosuccinimide (121 mg, 0.539 mmol) was added and the reaction mixture allowed to warm to room temperature overnight. After treatment with more triphenylphosphine (282 mg, 1.08 mmol) and N-iodosuccinimide (242 mg, 1.08 mmol), and stirring for a further 24 h, the reaction mixture was treated with aqueous methylamine (40%, 1.0 ml) and stirred for 5 h at room temperature. The reaction mixture was evaporated, the residue purified by reverse phase HPLC and the isolated product converted into the oxalate salt to give a colourless solid (37.2 mg, 16%).

MS APCI+ve$^m/z$ 343 ([M+H]$^+$).

$^1$H NMR 300 MHz (d$_6$-DMSO) 7.47 (1H, d), 7.43 (2H, d), 7.35 (2H, t), 7.24(1H, t), 6.87(1H, d), 6.78(1H, s), 6.28 (1H, d), 4.74 (1H, q), 2.96 (2H, m), 2.57 (3H, s), 2.36 (1H, m), 2.05(1H, m).

EXAMPLE 8

2-[[(1R)-3-Amino-1-phenylpropyl]amino]-4-chloro-5-fluorobenzonitrile a) 4-Chloro-5-fluoro-2-[[(1R)-3-hydroxy-1-phenylpropyl]amino]benzonitrile 4-Chloro-2,5-difluorobenzonitrile (1.0 g, 5.76 mmol) and (γ$^1$R)-γ-aminobenzenepropanol (870 mg, 5.76 mmol) were heated in N,N-diisopropylethylamine (740 mg, 5.76 mmol) at 140° C. for 30 h. The reaction mixture was partitioned between ethyl acetate and water and the organic layer separated. The aqueous layer was further extracted with ethyl acetate, and the extracts combined and dried over anhydrous sodium sulphate. The solvent was evaporated and the residue purified by flash chromatography using 10% ethyl acetate/isohexane as eluent to give the title product (260 mg, 15%).

MS APCI+ve$^m/z$ 305 ([M+H]$^+$).

$^1$H NMR 300 MHz (CDCl$_3$) 7.33 (5H, m), 7.15 (1H, d), 6.43 (1H, d), 5.98 (1H, d), 4.61 (1H, d), 3.79 (2H, m), 2.11 (2H, m).

b) 4-Chloro-5-fluoro-2-[[(1R)-3-iodo-1-phenylpropyl]amino]benzonitrile

The product of Example 8(a) (260 mg, 0.86 mmol) and triphenylphosphine (270 mg, 1.03 mmol) in dry tetrahydrofuran (15 ml) were cooled to 0° C. and treated with N-iodosuccinimide (230 mg, 1.03 mmol). The reaction mixture was stirred to room temperature overnight and divided for firer manipulation.

c) 2-[[(1R)-3-Azido-1-phenylpropyl]amino]-4-chloro-5-fluorobenzonitrile

Half of the crude solution from Example 8(b) was treated with sodium azide (59 mg, 0.9 mmol) in dry dimethylsulphoxide (5 ml) and stirred for 2 h at room temperature. The reaction mixture was partitioned between ethyl acetate and water and the organic layer separated. The aqueous was further extracted with ethyl acetate (2×) and the extracts combined, washed with brine and dried over anhydrous sodium sulphate. The solvent was evaporated and the crude product used for the next step.

d) 2-[[(1R)-3-Amino-1-phenylpropyl]amino]-4-chloro-5-fluorobenzonitrile hydrochloride The crude azide from Example 8(c) (108 mg) was dissolved in anhydrous methanol (10 ml), anhydrous stannous chloride (186 mg) was added and the reaction stirred for 1 h. The reaction mixture was filtered through celite and the filtrate concentrated to dryness. The residue was passed down a SCX ion exchange column initially using methanol as eluent and then aqueous ammonia to give an oil which was converted into the hydrochloride salt, giving a yellow solid (60 mg).

MS APCI+ve $^m$/z 304 ([M+H]$^+$).

$^1$H NMR 300 MHz (d$_6$-DMSO) 7.92 (3H, br s), 7.73 (1H, d), 7.47 (1H, d), 7.37 (2H, t), 7.27 (1H, t), 6.80 (2H, m), 4.74 (1H, q), 2.81 (2H, m), 2.14 (2H, m).

EXAMPLE 9

4-Chloro-5-fluoro-2-[[(1R)-3-(methylamino)-1-phenylpropyl]amino]benzonitrile hydrochloride Half of the crude solution from Example 8(b) was treated with 40% aqueous methylamine (0.06 ml) and the reaction mixture stirred overnight at room temperature. The mixture was concentrated and the residue passed down a SCX ion exchange column initially eluting with methanol then aqueous ammonia to give an oil which was converted into the hydrochloride salt to give a colourless foam (26 mg).

MS APCI+ve $^m$/z 318 ([M+H]$^+$).

$^1$H NMR 300 MHz (d$_6$-DMSO) 8.71 (1H, s), 7.73 (1H, d), 7.47(2H, d), 7.37 (2H, t), 7.27 (1H, t), 6.81 (2H, m), 4.76 (1H, m), 2.92 (2H, m), 2.55 (3H, s), 2.32 (1H, m), 2.05 (1H, m).

EXAMPLE 10

N-(5-Chloro-2-nitrophenyl)-1-phenyl-3-(morpholin-1-yl)propanamine fumarate

A mixture of 4-chloro-2-fluoronitrobenzene (900 mg, 5.13 mmol) and 1-phenyl-3-(morpholin-1-yl)propanamine (1.13 g, 5.13 mmol) in acetonitrile (50 ml) was heated under reflux for 2 h. The cooled reaction mixture was then quenched with 2N aqueous hydrochloric acid (200 ml), and the products extracted into diethyl ether (2×100 ml). The aqueous phase was collected, basified with solid potassium carbonate to pH 14, and extracted with ethyl acetate (2×150 ml). The combined extracts were dried over magnesium sulphate, filtered and concentrated to an oil. The crude product was purified on silica gel using ethyl acetate as eluent to give an oil (1 g, 52%). The amine was converted into the fumarate salt by addition of fumaric acid (1 equivalent) in ethanol (10 ml) and the product collected by filtration. After recrystallisation from ethanol, a yellow solid (380 mg, 18%) was obtained.

MS APCI+ve $^m$/z 376 ([M+H]$^+$).

$^1$H NMR 400 MHz (d$_6$-DMSO) 8.89 (1H, d), 8.09 (1H, d), 7.43–7.25 (5H, m), 6.84 (1H, d), 6.68 (1H, dd), 6.62 (2H, s), 4.96 (1H, dd), 3.69–3.63 (4H, m), 2.5–2.3 (6H, m), 2.15–1.97 (2H, m).

EXAMPLE 11

2-[[(1R)-3-Amino-1-phenylpropyl]thio]-4-chlorobenzonitrile fumarate a) α-(2-Azidoethyl)-(α$^1$S)-benzenemethanol (α$^1$S)-α-(2-Chloroethyl)benzenemethanol (1.68 g, 9.85 mmol) and sodium azide (960 mg, 1.5 eq.) in wet DMSO (15 ml+water 0.5 ml) were stirred and heated at 50° C. for 17 h. The reaction mixture was diluted with water (300 ml) and the products extracted into diethyl ether (2×200 ml). The combined extracts were dried (magnesium sulphate) and concentrated to an oil. Purification was achieved on silica gel eluting with 10% acetone/isohexane to afford the azide as a colourless oil (1.6 g, 92%).

$^1$H NMR 300 MHz (CDCl$_3$) 7.41–7.27 (5H, m), 4.88–4.82 (1H, m), 3.55–3.35 (2H, m), 2.11–1.89 (3H, m).

b) α-(2-Azidoethyl)-(α$^1$R)-benzenemethanethiol

To a solution of tris(4-chlorophenyl)phosphine (7.82 g, 21.4 mmol) in dry tetrahydrofuran was added diethyl azodicarboxylate (4 ml, 1.2 eq.), and the mixture stirred at ambient temperature for 15 minutes. The product of Example 11(a) (3.8 g, 21.4 mmol) was added to the mixture followed by thiobenzoic acid (2.96 g, 1 eq.). The resulting orange solution was stirred overnight. The mixture was then treated with sodium methoxide in methanol (10 ml, 25 wt %, 46 mmol). After 10 minutes the mixture was poured into water (100 ml) and made acidic by addition of 4M hydrochloric acid. The products were extracted into ethyl acetate (200 ml), and the extract dried (magnesium sulphate) and concentrated to a dark green oil. Purification was achieved on silica gel eluting with 1% ethyl acetate in isohexane and afforded the thiol as an orange oil (1.4 g, 34%).

$^1$H NMR 300 MHz (CDCl$_3$) 7.4–7.2 (5H, m), 4.12 (1H, q), 3.44–3.22 (2H, m), 2.24–2.1 (2H, m), 1.96 (1H, d).

c) 2-[[(1R)-3-Azido-1-phenylpropyl]thio]-4-chlorobenzonitrile

To a stirred solution of the product of Example 11(b) (620 mg, 3.2 mmol) and 4-chloro-2-fluorobenzonitrile (500 mg, 3.2 mmol) in dry tetrahydrofuran (20 ml) was added sodium hydride (130 mg, 60% dispersion in mineral oil, 3.2 mmol). The mixture was stirred at ambient temperature for 2 h, then diluted with water (150 ml). The products were extracted into diethyl ether (100 ml), and the extract dried (magnesium sulphate) and concentrated. The crude product was purified on silica gel eluting with 20% diethyl ether/isohexane and afforded the title compound as a colourless solid (500 mg, 48%).

$^1$H NMR 300 MHz (CDCl$_3$) 7.7–7.2 (8H, m), 4.52 (1H, dd), 3.53–3.24 (2H, m), 2.32–2.2 (2H, m).

d) 2-[[(1R)-3-Amino-1-phenylpropyl]thio]-4-chlorobenzonitrile fumarate

The azide of Example 11(c) (500 mg, 1.53 mmol) in tetrahydrofuran (30 ml) was treated with triphenylphosphine (600 mg, 2.3 mmol) and water (0.3 ml). The mixture was then stirred and heated under reflux for 1.5 h. The cooled solution was concentrated to dryness, and the residue purified on silica gel eluting with 10% 7N ammonia in methanol/dichloromethane. The amine was isolated as a colourless oil and was converted into a fumarate salt with 1 equivalent of fumaric acid in ethanol to give a colourless solid (490 mg, 51%).

MS APCI+ve $^m$/z 303 ([M+H]$^+$).

$^1$H NMR 400 MHz (d$_6$-DMSO) 7.82–7.25 (8H, m), 6.42 (~1.3H, s), 4.95 (1H, t), 2.83–2.63 (2H, m), 2.25–2.18 (2H, m).

EXAMPLE 12

2-[[(1R)-3-Amino-1-phenylpropyl]thio]-4-(trifluoromethyl)benzonitrile fumarate

The title compound was prepared in the same manner as Example 11 but using 2-fluoro-4-(trifluoromethyl)benzonitrile and was isolated as a fumarate salt (600 mg, 63%).

MS APCI+ve$^m$/z 337 ([M+H]$^+$).

$^1$H NMR 400 MHz (d$_6$-DMSO) 8.01 (1H, d), 7.83 (1H, s), 7.71 (1H, d), 7.4–7.22 (5H, m), 6.41 (~1.3H, s), 5.02 (1H, t), 2.85–2.67 (2H, m), 2.27–2.21 (2H, m).

EXAMPLE 13

γ-[(2,5-Dimethylphenyl)thio]-N-methyl-benzenepropanamine hydrochloride

Prepared by the procedure described in Example 1, but using 2,5-dimethylbenzenethiol and diisopropylethylamine (8.5 equivalents) in methanol in preference to sodium ethoxide. The amine was isolated as a hydrochloride salt by treatment with hydrogen chloride in diethyl ether.

MS APCI+ve$^m$/z 286 ([M+H]$^+$).

$^1$H NMR 300 MHz (d$_6$-DMSO) 8.87 (2H, br s), 7.35–6.94 (8H, m), 4.49 (1H, t), 2.96–2.86 (1H, m), 2.72–2.66 (1H, m), 2.48 (3H, s), 2.29–2.17 (8H, m).

EXAMPLE 14

4-Chloro-2-[methyl[3-(methylamino)-1-phenylpropyl]amino]benzonitrile oxalate a) 4-Chloro-2-[(3-hydroxy-1-phenylpropyl)amino]benzonitrile A mixture of 3-amino-3-phenylpropanol (1 g, 6.6 mmol) and 4-chloro-2-fluorobenzonitrile (1 g, 6.4 mmol) in diisopropylethylamine (1.2 ml, 6.9 mmol) was heated at 140° C. for 5 h. The crude reaction mixture was cooled to room temperature and applied to a silica column. The title compound was isolated as a colourless solid (1.1 g, 58%) by elution with 20% diethyl ether/isohexane.

MS APCI+ve$^m$/z 287 ([M+H]$^+$).

b) 4-Chloro-2-[[3-[[(1,1-dimethylethyl)dimethylsilyl]oxy]-1-phenylpropyl]amino]benzonitrile A solution of 4-chloro-2-[(3-hydroxy-1-phenylpropyl)amino]benzonitrile (2.3 g, 8 mmol) in dry tetrahydrofuran (50 ml) was treated with tert-butyldimethylsilylchloride (2.41 g, 2 eq.) and imidazole (1.09 g, 2 eq.) and stirred at room temperature for 1 h. The reaction mixture was diluted with water (200 ml) and the products extracted into diethyl ether (200 ml). The organic extract was dried over magnesium sulphate and concentrated to an oil. The crude product was purified on silica gel eluting with isohexane/diethyl ether (2:1) to afford the title compound as a colourless oil (2.3 g, 72%).

$^1$H NMR 400 MHz (CDCl$_3$) 7.35–7.15 (6H, m), 6.52 (1H, d), 6.41 (1H, s), 5.42(1H, d), 4.58 (1H, q), 3.7–3.5 (2H, m), 2.0 (2H, m), 0.83 (9H, s), 0.0 (6H, s).

c) 4-Chloro-2-[(3-hydroxy-1-phenylpropyl)methylamino]benzonitrile

To a stirred suspension of sodium hydride (60% dispersion, 270 mg, 6.75 mmol) in dry tetrahydrofuran (20 ml) under nitrogen and at 0° C. was added 4-chloro-2-[[3-[[(1,1-dimethylethyl)dimethylsilyl]oxy]-1-phenylpropyl]amino]benzonitrile (2.3 g, 5.74 mmol) in tetrahydrofuran (10 ml). The resulting yellow suspension was stirred at room temperature for 2 h, and then treated with methyl iodide (3.6 ml, 57.4 mmol). The resulting mixture was heated under reflux for 10 h, and then treated with acetic acid (10 ml) and water (2 ml). Heating and stirring were continued overnight. The mixture was concentrated under vacuum and the residue partitioned between water (50 ml) and ethyl acetate (100 ml). The organic extract was collected and dried over magnesium sulphate. After concentration of the extract the residue was purified on silica gel using 80% isohexane/diethyl ether as eluent. The title compound was isolated as a colourless oil (1 g, 58%).

$^1$H NMR 400 MHz (CDCl$_3$) 7.51–6.76 (8H, m), 5.13 (1H, t), 3.8–3.72 (2H, m), 2.69 (3H, s), 2.39–2.33 (2H, m).

d) 4-Chloro-2-[(3-chloro-1-phenylpropyl)methylamino]benzonitrile

4-Chloro-2-[(3-hydroxy-1-phenylpropyl)methylamino]benzonitrile (1 g, 3.3 mmol) was dissolved in thionyl chloride (10 ml). To the solution was added diisopropylethylamine (0.1 ml, 0.57 mmol) and the mixture stirred at room temperature for 15 minutes, then concentrated to dryness under vacuum. The crude material was purified on silica gel (eluting with 20% diethyl ether/isohexane) to afford the chloride as a colourless oil (330 mg, 31%).

GC/MS$^m$/z 318/20/22 ([M]$^+$).

e) 4-Chloro-2-[methyl[3-(methylamino)-1-phenylpropyl]amino]benzonitrile oxalate

4-Chloro-2-[(3-chloro-1-phenylpropyl)methylamino]benzonitrile (300 mg, 0.94 mmol) was dissolved in a saturated solution of methylamine in methanol (7 ml) and the mixture heated in a pressure vessel at 140° C. for 24 h. The mixture was concentrated, and the residue purified on a silica column eluting with 10% 7N ammonia in methanol/dichloromethane. The title compound was isolated as an oxalate salt (30 mg, 10%).

MS APCI+ve$^m$/z 314 ([M+H]$^+$).

$^1$H NMR 300 MHz (d$_6$-DMSO) 7.75 (1H, d), 7.45–6.98 (7H, m), 5.01 (1H, t), 3.0–2.8 (2H, m), 2.68 (3H, s), 2.56 (3H, s), 2.5–2.2 (2H, m).

EXAMPLE 15

(γ$^2$R)-γ-[(2,5-Dichlorophenyl)thio]-2-thiazolepropanamine hydrochloride a) [3-Oxo-3-(2-thiazolyl)propyl]carbamic acid 1,1-dimethylethyl ester To a solution of 2-bromothiazole (5.035 g, 30.7 mmol) in dry tetrahydrofuran (125 ml) at −78° C. under nitrogen, was added a solution of n-butyllithium in hexanes (1.6M, 17.6 ml, 28.2 mmol) over a period of 30 minutes, followed by a solution of [3-(methoxymethylamino)-3-oxopropyl]carbamic acid 1,1-dimethylethyl ester (2.976 g, 12.8 mmol) in dry tetrahydrofuran (30 ml) added over 30 minutes. The reaction mixture was allowed to warm up to 0° C., then quenched with saturated ammonium chloride and extracted with ethyl acetate (3×100 ml). The combined extracts were washed with water (3×50 ml) and saturated brine solution (1×100 ml), dried (magnesium sulphate) and concentrated in vacuo to leave a crude orange oil. Flash chromatography (silica, 25% ethyl acetate in isohexane) gave a pale yellow oil (2.2 g, 67%).

MS APCI+ve$^m$/z 201 ([M(−C$_4$H$_9$)(+H)]$^+$).

$^1$H NMR 300 MHz (CDCl$_3$) 8.01 (1H, m), 7.69 (1H, m), 5.05 (1H, br s), 3.57 (2H, q), 3.39 (2H, t), 1.46 (9H, s).

b) [(3S)-3-Hydroxy-3-(2-thiazolyl)propyl]carbamic acid 1,1-dimethylethyl ester

To a solution of (R)-3-methyl-CBS-oxazaborolidine (1M solution in toluene, 0.43 ml) in dry tetrahydrofuran (30 ml)

at −10° C. under nitrogen, was added borane-tetrahydrofuran complex (1M in tetrahydrofuran, 2.58 ml) and the mixture was stirred at −10° C. for 15 minutes. A solution of [3-oxo-3-(2-thiazolyl)propyl]carbamic acid 1,1-dimethylethyl ester (1.1 g, 4.3 mmol) in dry tetrahydrofuran (20 ml) was added dropwise over 45 minutes and the resulting mixture was allowed to warm up to room temperature over 16 h. Methanol (10 ml) was added and the mixture was stirred at room temperature for 15 minutes before the solvent was removed at reduced pressure. Methanol (10 ml) was again added and removed at reduced pressure to leave a crude yellow oil. Flash chromatography (silica, 25 to 100% ethyl acetate in isohexane) afforded a clear gum (0.74 g, 67%).

MS APCI+ve$^m$/z 259 [(M+H)$^+$].

c) [(3R)-3-[(2,5-Dichlorophenyl)thio]-3-(2-thiazolyl)propyl]carbamic acid 1,1-dimethylethyl ester.

To a solution of 2,5-dichlorothiophenol (179 mg, 1 mmol), [(3S)-3-hydroxy-3-(2-thiazolyl)propyl]carbamic acid 1,1-dimethylethyl ester (258 mg, 1 mmol) and triphenylphosphine (315 mg, 1.2 mmol) in dry tetrahydrofuran (30 ml) at 0° C. under nitrogen, was added diisopropyl azodicarboxylate (243 mg, 0.24 ml, 1.2 mmol) dropwise over 5 minutes. The mixture was stirred at room temperature for 16 h, then concentrated in vacuo to leave a crude yellow gum. Flash chromatography (silica, 15% ethyl acetate in isohexane) afforded a clear oil (85 mg, 21%).

MS APCI+ve$^m$/z 419/421/423 [(M+H)$^+$].

d) ($\gamma^2$R)-$\gamma$-[(2,5-Dichlorophenyl)thio]-2-thiazolepropanamine hydrochloride The product from Example 15(c) in dry dioxan (3 ml) was treated with 4M hydrochloric acid (1 ml) and the mixture stirred at room temperature for 16 h. The precipitate was collected, washed with ethyl acetate and vacuum dried to leave a white solid (39 mg, 54%).

MS APCI+ve$^m$/z 319/321 [(M+H)$^+$].

$^1$H NMR 300 MHz (d$_6$-DMSO) 8.06 (3H, bd s), 7.87 (1H, d), 7.80 (1H, d), 7.52 (1H, d), 7.36 (1H, d), 7.09 (1H, dd), 6.16 (1H, dd), 3.03–2.97 (2H, m), 2.45–2.33 (2H, m).

EXAMPLE 16

$\gamma$-[(2,5-Dichlorophenyl)thio]-2-oxazolepropanamine oxalate a) 3-Chloro-1-(2-oxazolyl)-1-propanone To a solution of oxazole (2.93 g, 42.5 mmol) in tetrahydrofuran (150 ml) at −70° C. under a nitrogen atmosphere was added n-butyllithium (2.5 M solution in hexanes, 17 ml) dropwise and the solution stirred for 20 minutes. Zinc chloride (1 M solution in diethyl ether, 84.9 ml) was added and the solution warmed to 0° C. over 45 minutes. Solid cuprous iodide (8.09 g, 42.5 mmol) was added and after 10 minutes, 3-chloropropionyl chloride (8.38 ml, 87.8 mmol) was added. After 1 h, ethyl acetate and aqueous ammonium chloride solution were added. The organic layer was separated and washed sequentially with aqueous ammonium chloride solution, water and brine. The solution was dried (sodium sulphate) and evaporated to yield the crude product as a red oil (15.5 g). This material was used without further purification.

$^1$H NMR 300 MHz (CDCl$_3$) 7.86 (1H, s), 7.36 (1H, s), 3.93 (2H, t), 3.57 (2H, m.

b) S-$\alpha$-(Azidoethyl)-2-oxazolemethanol (R)-2-Methyl-CBS-oxazaborolidine (1M solution in toluene, 1.41 ml) was added to tetrahydrofuran (14 ml) under a nitrogen atmosphere and the solution cooled to −5° C. Borane-tetrahydrofuran complex (1M solution in tetrahydrofuran, 14.1 ml) was added dropwise and the solution stirred for 10 minutes. A solution of the, crude product from Example 16(a) (ca. 14 mmol) in tetrahydrofuran (10 ml) was added dropwise and the reaction warmed slowly to 0° C. over 16 h. Methanol (40 ml) was cautiously added and the volatiles removed in vacuo. Two further methanol addition/solvent evaporation cycles were performed. The residue was purified by flash column chromatography using 5 to 30% ethyl acetate/isohexane as eluent to give a colourless oil (1.08 g). This material was taken up into dimethylsulfoxide (7 ml), solid sodium azide (604 mg) was added, and the reaction heated at 65° C. for 16 h. After cooling to room temperature, water was added and the solution extracted three times with diethyl ether. The combined organic extracts were dried (sodium sulfate) and the solvent removed in vacuo to yield the sub title compound (750 mg) as an orange oil. This material was used without further purification.

$^1$H NMR 300 MHz (CDCl$_3$) 7.65 (1H, d), 7.10 (1H, d), 4.96 (1H, dd), 3.53 (2H, m), 3.02 (1H, bs), 2.18 (2H, m).

c) $\gamma$-[(2,5-Dichlorophenyl)thio]-2-oxazolepropanamine oxalate

To a solution of triphenylphosphine (700 mg) in tetrahydrofuran (4 ml) at 0° C. was added diethyl azodicarboxylate (0.48 ml) dropwise. After 10 minutes, a solution of the product from Example 16(b) (0.32 g) and 2,5-dichlorobenzenethiol (340 mg) in tetrahydrofuran (4 ml) was added dropwise and the solution stirred at 0° C. for 30 minutes and then at room temperature for 16 h. Further triphenylphosphine (1 g) and water (3 ml) were added and the reaction stirred for 16 h. Purification by flash chromatography on SCX resin using 0 to 7N ammonia in methanol as eluent followed by further purification by RP-HPLC gave the free base of the title product as a yellow foam (196 mg). This material was taken up in methanol and oxalic acid (1 eq.) in diethyl ether (1 ml) added. The solvent was removed in vacuo, and the residue washed with ethyl acetate. The resulting solid was dried in vacuo to yield the title product (117 mg) as a white solid.

MS APCI+ve$^m$/z 303 [(M+H)$^+$].

$^1$H NMR 400 MHz (d$_4$-MeOH) 7.91 (1H, s), 7.48 (2H, m), 7.35 (1H, dd), 7.15 (1H, s), 4.75 (1H, t), 3.27–3.20 (1H, m), 3.12–3.05 (1H, m), 2.55–2.39 (2H, m).

SCREENS

The pharmacological activity of compounds according to the invention was tested in the following screens.

Screen 1

The activity of compounds of formula (I), or a pharmaceutically acceptable salt, enantiomer or racemate thereof, may be screened for nitric oxide synthase inhibiting activity by a procedure based on that of Förstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund).

J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% $CO_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM tris-HCl (pH 7.5 at 20° C.), 10% (v/v) glycerol, 0.1% (v/v) triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 µl of substrate cocktail (50 mM tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 mCi L-[$^3$H] arginine) is added to wells of a 96 well filter plate (0.45 µM pore size) containing 25 µl of a solution of test compound in 50 mM tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA. Labelled L-citrulline is separated from labelled L-arginine using Dowex AG-50W. 150 µl of a 25% aqueous slurry of Dowex 50W (Na$^+$ form) is added to the assay after which the whole is filtered into 96 well plates. 75 µl of filtrate is sampled and added to wells of 96 well plates containing solid scintillant. After allowing the samples to dry the L-citrulline is quantified by scintillation counting.

In a typical experiment basal activity is 300 dpm per 75 µl sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 µM, is tested as a standard to verify the procedure. Compounds are tested at a range of concentrations and from the inhibitions obtained $IC_{50}$ values are calculated. Compounds that inhibit the enzyme by at least 25% at 100 µM are classed as being active and are subjected to at least one retest.

Screen 2

Compounds also show activity against the human form of induced nitric oxide synthase as can be demonstrated in the following assay.

Enzyme is prepared, after induction, from the cultured human colon adrenocarcinoma cell line DLD1 (obtained from the European Collection of Animal Cell Culture—cell line number 90102540). DLD1 cells are cultured in RPMI 1640 medium supplemented with 10% foetal bovine serum, 4 mM L-glutamine and antibiotics (100 units/ml penicillin G, 100 µg/ml streptomycin and 0.25 µg/ml amphotericin B). Cells are routinely grown in 225 cm$^3$ flasks containing 35 ml medium kept at 37° C. and in a humidified atmosphere containing 5% $CO_2$.

Nitric oxide synthase is produced by cells in response to interferon-γ (IFN-γ) and interleukin-1β (IL-1β). The medium from confluent flasks is removed and replaced with 25 ml (per flask) of fresh medium containing 250 units/ml IL-1β and 1000 units/ml IFN-γ. After a period of 17–20 hours in culture, harvesting of cells is accomplished by scraping the cell monolayer from the flask surface into the culture medium. Cells are collected by centrifugation (1000 g for 10 minutes) and lysate prepared by adding to the cell pellet a solution containing 50 mM tris-HCl (pH 7.5 at 20° C.), 10% (v/v) glycerol, 0.1% (v/v) triton-X100, 0.1 mM dithiothreitol and a cocktail of protease inhibitors including leupeptin (2 µg/ml), soya bean trypsin inhibitor (10 µg/ml), aprotonin (5 µg/ml) and phenylmethylsulphonyl fluoride (50 µg/ml).

For the assay, 25 µl of substrate cocktail (50 mM tris-HCl (pH 7.5), 400 µM NADPH, 20 µM flavin adenine dinucleotide, 20 µM flavin mononucleotide and 4 µM tetrahydrobiopterin) is added to the wells of a 96-well plate. Test compounds are preincubated with enzyme by adding together with 40 µl of cell lysate (prepared as above) and incubating for 1 hour at 37° C. at the end of which period 10 µl of 30 µM L-arginine and 0.025 µCi of L-[$^3$H]-arginine in 50 mM tris-HCl is added to start the enzymatic reaction. Incubation is continued for a further 1 hour at 37° C. The reaction is terminated by addition of 50 µl of an aqueous solution of 3 mM nitroarginine and 21 mM EDTA.

Labelled L-citrulline is separated from labelled L-arginine using Dowex AG-50W. 120 µl of a 25% aqueous slurry of Dowex 50W is added to 96 well filter plates (0.45 µm pore size). To this is added 120 µl of terminated assay mix. 75 µl of filtrate is sampled and added to the wells of 96 well plates containing solid scintillant. After allowing the samples to dry the L-citrulline is quantified by scintillation counting.

In a typical experiment basal activity is 300 dpm per 75 µl sample of reagent controls, which is increased to 3000 dpm in the presence of enzyme. Compound activity is expressed as $IC_{50}$ (the concentration of drug substance which gives 50% enzyme inhibition in the assay) and L-NMMA, which gives an $IC_{50}$ of about 0.4 µM is tested as a standard to verify the procedure. Compounds are tested at a range of concentrations and from the inhibitions obtained $IC_{50}$ values are calculated.

When tested, the compounds of Examples 1 to 16 gave $IC_{50}$ values of less than 15 µM in at least one of the above screens, indicating that they are predicted to show useful therapeutic activity.

What is claimed is:

1. A method of treating, or reducing the risk of, inflammatory disease in a person suffering from, or at risk of, said disease, wherein the method comprises administering to the person a therapeutically effective amount of a compound of formula (I),

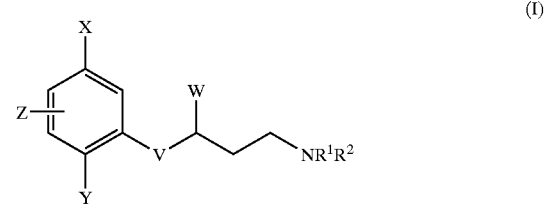

wherein:
X and Y independently represent C1 to 4 alkyl, C1 to 4 alkoxy, halogen, $CF_3$, $OCF_3$, CN, C≡H, $S(O)_mCH_3$, $S(O)_pCF_3$, $NO_2$ or NHCHO;

m and p independently represent an integer 0, 1 or 2;

Z represents H or fluoro;

V represents $S(O)_n$ or $NR^3$;

W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;

$R^3$ represents H or C1 to 4 alkyl;

$R^4$, $R^5$ $R^6$, $R^7$, $R^9$ and $R^{10}$ independently represent H or C1 to 4 alkyl;

$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

$R^{11}$ and $R^{12}$ independently represent H or C1 to 4 alkyl;

n represents an integer 0, 1 or 2;

or a pharmaceutically acceptable salt, enantiomer or racemate thereof, wherein the inflammatory disease is selected from the group consisting of inflammatory bowel disease, rheumatoid arthritis, osteoarthritis, chronic obstructive pulmonary disease and pain.

2. A compound of formula (Ia)

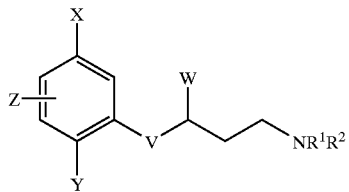

(Ia)

wherein

X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;

m and p independently represent an integer 0, 1 or 2;

Z represents H or fluoro;

V represents $S(O)_n$ or $NR^3$;

W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;

$R^3$ represents H or C1 to 4 alkyl;

$R^4$, $R^5$ $R^6$, $R^7$, $R^9$ and $R^{10}$ independently represent H or C1 to 4 alkyl;

$R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 ailcoxy, $CF_3$, $OCF_3$, CN or $NO_2$;

$R^{11}$ and $R^{12}$ independently represent H or C1 to 4 alkyl;

n represents an integer 0, 1 or 2;

or a pharmaceutically acceptable salt, enantiomer or racemate thereof, with the proviso that when V represents $S(O)_n$; and $R^1$ and $R^2$ independently represent H or methyl; and W represents phenyl, optionally substituted by halogen, C1 to 4 alkyl, C1 to 3 alkoxy or $CF_3$; or W represents thienyl, halothienyl, (C1 to 4 alkyl)-substituted-thienyl, furanyl, pyridyl or thiazolyl; then at least one of X and Y represents $OCF_3$, CN, C≡CH, $S(O)_mCH_3$, $S(O)_pCF_3$, $NO_2$ or NHCHO.

3. A compound of formula (1a), according to claim 2, wherein V represents S or NH.

4. A compound of formula (Ia), according to claim 2, wherein X and Y independently represent Br, Cl, $CH_3$, $CF_3$ or CN.

5. A compound of formula (Ia), according to claim 2, wherein the substituents $R^1$ and $R^2$ are independently H or $CF_3$.

6. A compound of formula (Ia), according to claim 2, which is:

2-[[3-(dimethylamino)-1-phenylpropyl]amino]-4-(trifluoromethyl)-benzonitrile;

4-chloro-2-[3-(methylamino)-1-phenylpropyl]amino]-benzonitrile;

4-chloro-2-{[3-(methylamino)-1-phenylpropyl]thio}benzonitrile;

4-bromo-2-{[3-(methylamino)-1-phenylpropyl]thio}benzonitrile;

(1R)-N1-[2-chloro-5-(trifluoromethyl)phenyl]N3-methyl-1-phenyl-1,3-propanediamine;

2-[[(1R)-3-amino-1-phenylpropyl]amino]-4-chloro-5-fluorobenzonitrile;

4-chloro-5-fluoro-2-[[(1R)-3-(methylamino)-1-phenylpropyl]amino]benzonitrile;
N-(5-chloro-2-nitrophenyl)-1-phenyl-3-(morpholin-1-yl)propanamine;
2-[[(1R)-3-amino-1-phenylpropyl]thio]-4-chlorobenzonitrile;
2-[[(1R)-3-amino-1-phenylpropyl]thio]-4-(trifluoromethyl)benzonitrile;
4-chloro-2-[methyl[3-(methylamino)-1-phenylpropyl]amino]benzonitrile;

g-[(2,5-dichlorophenyl)thio]-2-oxazolepropanamine;

or a pharmaceutically acceptable salt, enantiomer or racemate thereof.

7. A pharmaceutical composition comprising a compound of formula (Ia) according to claim 2, or a pharmaceutically acceptable salt, enantiomer or racemate thereof, in admixture with a pharmaceutically acceptable adjuvant, diluent or carrier.

* * * * *